United States Patent [19]

Entis et al.

[11] Patent Number: 5,168,037
[45] Date of Patent: Dec. 1, 1992

[54] METHOD FOR THE PREPARATION OF A LABELLED VIRUS WITHOUT THE INACTIVATION OF VIRAL BINDING SITES AND METHOD OF ASSAY UTILIZING SAID LABELLED VIRUS

[76] Inventors: Phyllis Entis; Michael P. Entis, both of 114 Spinnaker Ct., Del Mar, Calif. 92014

[21] Appl. No.: 561,756

[22] Filed: Aug. 2, 1990

[51] Int. Cl.$^5$ .............................................. C17Q 1/00
[52] U.S. Cl. ......................................... 435/5; 422/58; 435/30; 435/34; 435/39; 435/296; 436/536; 436/538; 436/805; 436/824
[58] Field of Search ................. 422/58; 435/5, 30, 34, 435/39, 296; 436/536, 538, 824, 805

[56] References Cited

U.S. PATENT DOCUMENTS

| | | |
|---|---|---|
| 3,717,705 | 2/1973 | Haimovich et al. |
| 4,104,126 | 8/1978 | Young .................................... 435/5 |
| 4,281,061 | 4/1981 | Zuk et al. ............................... 435/5 |
| 4,282,315 | 4/1981 | Luderer et al. ......................... 435/5 |
| 4,727,019 | 2/1988 | Valkirs et al. .......................... 435/5 |
| 4,797,363 | 1/1989 | Teodorescu et al. ................... 435/5 |
| 4,818,677 | 4/1989 | Hay-Kaufman et al. ............. 422/58 |
| 4,912,034 | 3/1990 | Kalra et al. ........................... 422/58 |
| 4,975,532 | 12/1990 | Rowley et al. ....................... 436/529 |

FOREIGN PATENT DOCUMENTS 8804326  6/1988  PCT Int'l Appl. .................... 435/34

OTHER PUBLICATIONS

Stanier et al., "*The Microbial World*", 5th Edition, (Prentice Hall, New Jersey), 1986, pp. 214–217.
"Detection of Food Pathogens Using the Phage Rapid Identification Assay System," a poster session presentation at the Institute of Food Technologists Annual Meeting in Jun. 1987.

*Primary Examiner*—Robert J. Hill, Jr.
*Assistant Examiner*—Christopher L. Chin

[57] ABSTRACT

A method for the preparation of a labelled target-specific virus where the binding sites on the virus are not inactivated by the label material. And a three-step process for detection of a targeted microorganism, the first step comprising contacting of labelled target-specific virus with a sample suspected of containing a target microorganism, the second step comprising the capture of the labelled virus/microorganism complexes onto a solid matrix, and the third step comprising the detection of said complexes on the solid matrix. The process is highly sensitive and can be used for rapid detection of target microorganisms in clinical, food, pharmaceutical, cosmetic and environmental samples. The invention further concerns a device and a kit based on the inventive process.

21 Claims, 1 Drawing Sheet

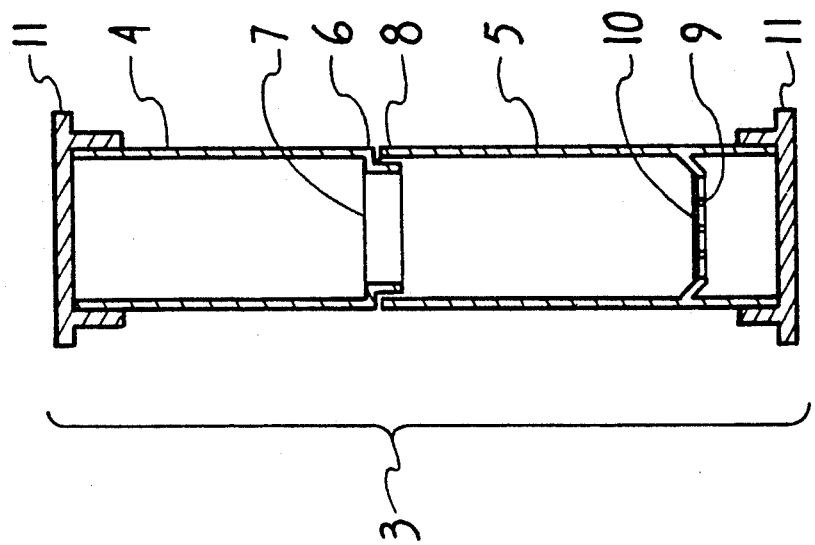
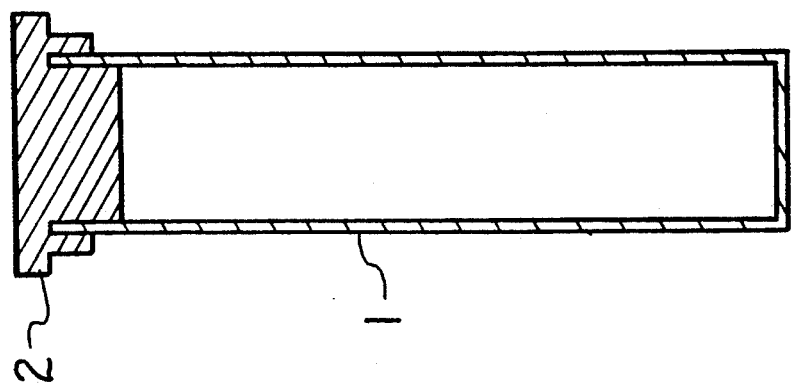

METHOD FOR THE PREPARATION OF A LABELLED VIRUS WITHOUT THE INACTIVATION OF VIRAL BINDING SITES AND METHOD OF ASSAY UTILIZING SAID LABELLED VIRUS

FIELD OF THE INVENTION

The present invention relates to a three-step process for detection of a targeted microorganisms, the first step comprising contacting labelled target-specific virus with a sample suspected of containing a target microorganism, the second step comprising the capture of the labelled virus/microorganism complexes onto a solid matrix, and the third step comprising the detection of said complexes on the solid matrix. The process is highly sensitive (i.e. able to detect very low numbers of target microorganisms) and can be used for rapid detection of target microorganisms in clinical, food, pharmaceutical, cosmetic and environmental samples. The invention further concerns a device and a kit based on the inventive process.

BACKGROUND OF THE INVENTION

Most procedures in use today for detection of specific microorganisms are based on principles developed in the 19th century for the diagnosis of microbial infections. Initially used in medical bacteriology, these traditional methods were later adapted to detect low levels of microbial contaminants in foods, pharmaceuticals, cosmetics and the environment.

In brief, these traditional methods incorporate the following steps:

(a) Primary Enrichment

Suspend all or part of the sample in a liquid nutrient medium and incubate one or more days to allow growth of all microorganisms contained in the sample, including the target microorganisms.

(b) Secondary Enrichment

Subculture a portion of the incubated primary enrichment into one or more secondary enrichment liquid culture media (formulated to encourage growth of the target microorganisms while suppressing many of the competing microorganisms) and incubate one or more days ("selective enrichment").

(c) Primary Isolation

Subculture a small portion of the incubated secondary enrichment media onto the surface of one or more solid selective culture media ("selective agar media") and incubate one or more days to enable development of isolated colonies of the target microorganisms.

(d) Purification

Subculture material from individual colonies from the selective agar media to fresh agar media to ensure that each colony selected for subculture and identification represents a pure culture of microorganisms.

(e) Identification

Inoculate the purified microbial culture into a panel of culture media designed to establish the physiological and biochemical characteristics of the microorganisms; also, where appropriate, determine the antigenic profile of the culture to complete the identification.

This basic approach philosophy is the same regardless of whether clinical specimens or food, pharmaceutical, cosmetics or environmental samples are tested. The duration and number of enrichment steps depend on the target microorganisms, the origin of the specimen and the desired method sensitivity (i.e.. to detect a lower concentration of target microorganisms in the sample, one usually increases the sample size and might also extend the primary and/or secondary enrichment periods). The choice of culture media depends almost exclusively on the target microorganisms.

This traditional approach to detect specific target microorganisms has several drawbacks. For example:

(1) The procedure requires several days to complete; the medical profession, however, demands rapid results for optimum patient treatment. Likewise, industry requires rapid screening so that raw materials can be released without delay for use in production, and so that finished products can be released for sale in a timely fashion.

(2) Growth of target microorganisms in the enrichment media can be unpredictable.
 (a) The presence of fast-growing non-target microorganisms can interfere with growth of the target microorganisms and mask their presence.
 (b) Microorganisms often sustain structural and/or physiological damage while in the sample and may require a relatively long period to repair these injuries before initiating growth.
 (c) Some samples contain substances inhibitory to microbial growth. These substances are introduced into the primary enrichment media together with the sample and may be present in high enough concentrations to slow or even prevent growth of the target microorganisms.

A number of alternative methods for detection of target microorganisms have been developed recently. These alternative methods include fluorescent antibody tests, enzyme linked immunosorbent assay ("ELISA") using either polyclonal or monoclonal antibodies, and nucleic acid probe assays.

For example, U.S. Pat. No. 4,376,110 describes two-site immunometric assays using pairs of monoclonal antibodies, one bound to a solid phase and the other labelled to permit detection. U.S. Pat. No. 4,514,508 employs a similar approach, but uses labelled complement to detect the antigen-antibody complex. U.S. Pat. No. 4,281,061 (Zuk et. al) describes a double antibody type detection method. Undesirable stearic effects are reduced by the introduction of the second antibody, thus sensitivity is increased and immunoassays with lower concentrations of target material including viruses and bacteria such as Salmonella can be performed. U.S. Pat. No. 4,659,678 (Forrest et al.) describes a triple-antibody immunoassay in which at least one of the antibodies must be monoclonal and another of the antibodies is fixed to a solid support.

However, to detect target microorganisms reliably, ELISA methods require a minimum concentration of 1,000,000 cells/mL; nucleic acid probes require 5,000,000 cells/mL and fluorescent antibody tests require 100,000 cells/mL.

All of these methods depend on an additional (tertiary) enrichment step following secondary enrichment to ensure the presence of an adequate concentration of target microorganisms in the enrichment broth. All of these alternative methods allow negative samples to be detected more rapidly by eliminating the need for primary isolation and purification. However, they do not eliminate the disadvantages associated with the enrichment steps. In fact, the need for a third enrichment might even increase the possibility of non-target microorganisms masking the presence of the target microorganisms. All three of these alternative methods, which kill the target microorganisms during the detection procedure, provide a negative screen result in about 48 hours (i.e. negative result can be believed, but positive result must be confirmed by traditional means). However, if a presumptive positive reaction develops, the secondary and tertiary enrichment cultures must be subcultured to obtain live microorganisms for confirmation and steps 3-5 of the traditional method must be carried out. Thus, confirmation of a positive result can take an additional 3-5 days. On the average, 5% of positive results reported by these alternative methods cannot be confirmed ("false positive").

Another alternative method, based on use of the hydrophobic grid membrane filter (U.S. Pat. No. 3,929,583), is also in use. This method can detect as few as 10 cells/mL present in the secondary enrichment culture. In the hydrophobic grid membrane filter ("HGMF") method, primary enrichment is carried out for 18-24 hours; secondary enrichment is reduced to 6 hours and a portion of the secondary enrichment culture is filtered through an HGMF and placed on a primary isolation medium for overnight incubation. The hydrophobic grid pattern serves to isolate and separate the colonies that develop on the HGMF surface and the selective and differential agents contained in the primary isolation medium provide a high degree of specificity to the reaction. The negative screen result is available in as little as 42 hours and, since living isolated colonies have already developed on the HGMF, confirmation can be obtained the following day versus 3-5 days for the other alternative methods described above. The false positive rate of the HGMF method is less than 1%.

While the HGMF method has significant advantages over both the traditional method and the other alternative methods, it still requires a minimum of 42 hours for a negative screen result. It would be of great benefit in both the clinical and industrial sectors to have a result available the same day that a sample has been submitted for analysis. A same-day test would, for example, allow some of the more common clinical diagnostic tests (such as detecting urinary tract infections) to be carried out right in the doctor's office.

None of the alternative methods described above have the sensitivity (i.e. ability to detect very low numbers of target microorganisms) to be adapted to a same-day test.

U.S. Pat. No. 4,547,466 (Turanchik et al.) describes the use of latex particles coated with antigen to detect antibody. The detection method consists of visual observation of particle agglutination, and the method can only be used with small sample volumes. U.S. Pat. No. 4,727,019 (Valkirs et al.) and U.S. Pat. No. 4,818,677 (Hay-Kaufman et al.) describe flow-through devices to capture target molecules or cells in an immunoassay test. In both cases, the flow-through capture element consists of a microporous filter material coated with a receptor molecule. Flow of the liquid through the microporous filter is achieved by capillary flow, rather than differential pressure, and all steps in the assay are carried out sequentially on the surface of the microporous filter. The nature of these devices would preclude the use of large sample volumes or materials containing particles (food or cosmetics, for example), as the filter material would rapidly become clogged. The sample volume capacity of U.S. Pat. No. 4,727,019 is further limited by the fluid-handling capacity of the absorbent material contained therein.

U.S. Pat. No. 4,254,082 (Schick et al.) describes a flow-through device incorporating a particulate adsorption material such as ion exchange, The target material (e.g., antigen) is captured by the adsorbent particles through non-specific attraction. A labelled detector molecule specific to the target (e.g., antibody) is then introduced. Lack of specificity in the initial capture step would make very difficult the capture of low numbers of targets in the presence of high numbers of competing materials, such as would occur in food sample homogenates or enrichments. Also, particle-containing samples would clog the device, preventing its use for large sample volumes.

U.S. Pat. No. 4,320,087 (Chau et al.) describes a device consisting of an activated-charcoal coated bead contained inside a specially designed test tube, such that the opening of the test tube is too small to permit removal of the bead. This device, likewise, cannot be used for large sample volumes and is a completely non-specific capture system.

Thus, there is a need for a highly sensitive process which can be used for rapid detection of target microorganisms in clinical, food, pharmaceutical, cosmetic and environmental samples.

SUMMARY OF THE INVENTION

The object of the present invention is to provide a method for producing a labelled virus without inactivating the virus' active binding sites and a rapid, highly-specific detection process. The detection system should detect bacteria, mycoplasma, fungi or protozoa in clinical, food, pharmaceutical, cosmetic and environmental samples.

A further object of the invention is to provide a detection system which is rapid, highly sensitive and highly specific for target microorganisms such as bacteria including Salmonella, Pseudomonas, Listerla, Yersinia, Neisseria, Staphylococcus, Streptococcus, *Escherichia coli,* Campylobacter, Legionella and Chlamydia; mycoplasma, including *Mycoplasma pneumoniae;* fungi, including Blastomyces, Histoplasma, Cryptococcus, Candida, Saccharomyces and Aspergillus; and protozoa including Giardia, Trypanosoma, Leishmania, Plasmodium and Toxoplasma.

A further objective of this invention is to circumvent the problems inherent in the traditional and alternative methods of detection of target microorganisms.

These and other objects are attained by the present new, rapid, highly sensitive and targeted detection system making use of a three-step process; the first step of a preferred embodiment comprising the formation of labelled target-specific virus/target microorganism complexes directly in a liquid sample or homogenate of a solid sample, the second step of a preferred embodiment comprising the capture of the labelled virus/microorganism complexes on a solid matrix, and the third step comprising detecting these complexes on the solid matrix. The invention is practiced in conjunction with a specially designed reaction vial and capture vial.

A more preferred embodiment of the invention thus comprises a process for detection of specific microorganisms comprising:

(a) contacting a labelled target-specific virus with a fluid to be tested for the presence of a target microorganism for a time sufficient to permit binding of the said virus with said target microorganism, if present;

(b) collecting labelled virus/target microorganism complexes obtained in (a) on a solid phase;

(c) draining the fluid and washing the solid phase to remove everything other than labelled virus/target microorganism complexes; and (d) determining presence of labelled virus on the solid phase.

BRIEF DESCRIPTION OF THE DRAWINGS

FIG. 1 shows an example of a reaction vessel which is exemplified by a test tube of sufficient capacity and having a suitable sealing plug or cap.

FIG. 2 shows a capture vessel consisting of a releasable upper portion containing a filter cloth for removal of visible particulates and a lower portion containing a capture filter.

DETAILED DESCRIPTION OF THE INVENTION

The present invention relates to a rapid and highly sensitive three-step process for detection of a targeted microorganism, the first step comprising the formation of labelled target-specific virus/target microorganism complexes directly in a liquid sample or homogenate of a solid sample, the second step comprising the capture of the labelled virus/microorganism complexes on a solid matrix, and the third step comprising detecting these complexes on the solid matrix.

The process of the present invention, by using a labelled target-specific virus as the first step of the detection system, achieves a very high ratio of label to target ("amplification"). For example, as many as 100 bacterial viruses ("bacteriophages") can attach to a single bacterial cell. Further, because viruses are much larger than other detectors in use (such as antibodies or nucleic acid probes), many more molecules of label material can be attached to each detector. This allows a very high degree of amplification of the detection signal.

Due to the high specificity and sensitivity of the present invention, it becomes possible to detect the target microorganism directly in the specimen or an aqueous homogenate of the specimen. i.e., without the conventional enrichment steps. This elimination of the enrichment steps results in great rapidity of the process.

There is, however, no impediment to enrichment of the sample, and one or more enrichment(s) may be employed after which the test will be applied to the enrichment culture. In a second embodiment of this invention, the procedure is carried out on an enrichment culture of the sample.

The use of phage as a tool in various microbiology techniques is not new. U.S. Pat. No. 3,717,705 (Haimovich et al.) attaches antigenic proteins to phage, mixes the phage with antibodies to those proteins and then tests the ability of the phage to infect and kill their normal host microorganism. In U.S. Pat. No. 4,104,126, phage are used to lyse their normal host bacteria to enable the contents of the bacterial cells to be recovered and analyzed. U.S. Pat. No. 4,282,315 (Luderer et al.) describes a process for selecting a particular subpopulation of viruses. U.S. Pat. No. 4,797,363 (Teodorescu et al.) uses mutated bacteriophages coated with antibodies as agents for recognition of molecules and cellular materials. In the practice of the procedure taught in this patent the target-specific virus may be selected to bind through its head or through its tail. In the latter instance, this is accomplished by "external imaging" whereby the bacteriophage is modified to perform in the manner of an antibody. However, none of these patents disclose or suggest the use of a labelled virus to detect specific target microorganisms at very low concentrations in clinical, food, pharmaceutical, cosmetic or environmental samples.

Various signal producing systems can be employed in consideration of labelling the virus in the present invention. Signal producing systems capable of generating a detectable visual change on the surface of the solid substrate include color-generating systems, fluorescent systems, and luminescent systems. Suitable signal producing systems will include at least one component and may comprise two or more components including an enzyme, such as horseradish peroxidase, a substrate, a catalyst, an enhancer a fluorescent dye, a chemiluminescent dye, radioactive label or any other label capable of being directly or indirectly detected visually or by instrument. Numerous suitable signal producing systems are described in U.S. Pat. No. 4,366,241, the disclosure of which is incorporated herein by reference.

The virus may be made radioactive either by incorporation of radioactive materials in its protein or nucleic acid or by conventional procedures of coupling radioactive materials to proteins. In the alternative, a metal such as silver is added to the virus by conventional procedures.

U.S. Pat. No. 3,717,705 and 4,104,126 employ a wide variety of conjugation techniques to link various proteins to bacterial viruses ("phages"). The techniques employed create a link between two amine groups (e.g., using glutaraldehyde bridging) or between some other functional group and either an amine or a carboxyl group on the phage. The ability of phages to recognize and attach to their specific host depends on the active sites on the phages (either amino or carboxyl groups) recognizing and binding to complementary sites on the bacterial cell wall. Use of these same active groups as targets for protein binding, without protecting the specific host recognition sites will result in significant phage inactivation attributable to interference with the attachment mechanism. For example, glutaraldehyde employed to conjugate phages will, to some extent, cross-link adjoining tail fibers of the phages or, indeed, bridge one phage to another, thus inactivating both phages. U.S. Pat. No. 3,717,705 reported phage activity survival following protein labelling of at little as 0.05% of the initial active population.

In contrast to U.S. Pat. No. 3,717,705 and 4,104,126, the present invention is predicated on the use of intensely labelled virus particles which have retained high specific attachment activity to the target microorganism. To achieve this, the labelling process of the present invention specifically protects the attachment recognition sites on the virus by introducing a different active functional group onto the virus for the purpose of attachment of signal-producing molecules to the virus.

When an enzyme is used as part of the signal-producing system for the target-specific virus, the enzyme may be any conventional enzyme such as an oxidoreductase, transferase, hydrolase, lyase, isomerase ligase or synthetase. Specific enzymes and the manner of their employment in signal producing systems are described, for example in columns 14–21 of U.S. Pat. No. 4,281,061 (Zuk et al.). Other combinations of enzyme and substrate systems are also included in the scope of this invention.

The components of the kit will now be described in detail with reference to the appropriate Figures.

FIG. 1—Reaction Vial

FIG. 1 shows an example of a vial 1 with a friction fit plug 2. This vial may be made of any suitable material such as, but not limited to, glass or plastic. It should be of sufficient capacity to allow a fluid sample suspected of possibly containing a target microorganism together with the labelled target-specific virus to react with one another for the purpose of forming labelled virus/target microorganism complexes. Therefore, this Reaction Vial would normally have a capacity of at least 10 milliliters. The preferred embodiment of this device would be a test tube of suitable capacity containing lyophilized labelled target-specific virus.

FIG. 2—Capture Vial

FIG. 2 illustrates a tubular type device comprising a detachable upper chamber containing a filter cloth capable of removing visible particulates and a lower chamber containing a capture filter material capable of capturing labelled target-specific virus/target microorganism complexes while allowing non-complexed labelled target-specific virus to flow therethrough. This device contains a cap or plug at both the top and bottom ends to ensure integrity of the device prior to use.

The main body of this device can be of any shape or form such as a clear plastic cylinder (FIG. 2). Ideally this cylinder will be dimensioned so that it can be easily hand-held and of a sufficient internal diameter as to allow fluids to be poured into the top of the cylinder.

The cylinder main body 3 is comprised of two detachable bodies, an upper body 4 and a lower body 5.

Located within upper body 4 is a solid phase retaining means such as a perimeter shelf 6. This shelf 6 is likely an integral part of the upper body 4, having been molded at the same time as the upper body. To this shelf 6 is affixed a filter cloth 7 capable of trapping visible particulates while allowing the balance of fluids to pass therethrough. The filter cloth 7 is ideally a woven sieve-like material made of polyester, nylon or other suitable materials. The filter cloth 7 should have a porosity of at least 5 microns to permit everything but visible particulates to flow therethrough. This filter cloth 7 can be heat or ultrasonically welded to the shelf 6 in upper body 4.

The upper body 4 is releasably connected to lower body 5 by means of a fitted nesting 8 or such other means, such as a threaded fitting, all of which is intended to allow fluids to be retained within the main body 3 while passing from upper body 4 to lower body 5.

Located within lower body 5 is a solid phase retaining means such as a perforated platform or grate 9. This grate 9 may be an integral part of lower body 5 having been molded at the same time as lower body 5. The openings in this grate 9 are sufficiently large to allow fluids to pass therethrough.

Situated on grate 9 is a capture filter material 10 having characteristics of porosity and protein binding such as to capture any labelled target-specific virus/target microorganism complexes while allowing non-complexed labelled target-specific virus to pass therethrough. The capture filter material 10 may ideally be a membrane filter having a porosity equal to or greater than 0.45 microns and low in protein binding properties. The capture filter material 10 can be affixed to grate 9 at the circumference of capture filter material 10 by means of heat welding or such other means as will preserve the inherent hydrophilic or fluid transmission properties of capture filter material 10.

To retain the integrity of the reaction vial prior to use, it may be fitted both at the top and bottom with friction fit caps 11 made of a soft plastic such as polyethylene or polypropylene or some suitable alternative material. In an alternative embodiment, one or both of the friction fit caps are replaced by a detachable plug or lid.

The present invention is useful in assaying for a wide variety of target microorganisms in virtually any type of sample which is liquid, which can be liquified, or which can be suspended in a liquid. The process and device will find use with biological specimens, such as blood, serum, plasma, urine, cerebral fluid, spinal fluid, ocular lens liquid (tears), saliva, sputum, semen, cervical mucus, scrapings, swab samples and the like. Use will also be found with industrial, environmental and food samples, such as aviation fuels, lubricants, water, process streams, milk, meat, poultry, fish and the like. Under certain circumstances, it may be desirable to pretreat the sample, such as by liquification, separation, dilution, concentration, filtration, chemical treatment, or a combination thereof, in order to improve the compatibility of the sample with the assay. The selection of pretreatments for biological, industrial, and environmental samples is well-known in the art and need not be described further.

The method and kit of the present invention are particularly useful for the performance of assays by untrained and semi-trained individuals. Sample preparation is usually minimal, and the assay method steps may be easily performed by an individual reading a set of instructions accompanying the assay kit. The enhanced sensitivity and readability of the assay are particularly helpful in assuring that the test results are easily read and understood even by untrained persons.

DETAILED DESCRIPTION OF THE PREFERRED EMBODIMENT

The present invention may be applied to the detection of any target microorganism for which a target-specific virus can be obtained. For illustrative purposes, the present invention will be described using as an example the rapid detection of Salmonella spp. The scope of the invention is not limited to Salmonella spp.; choice of the correct labelled target-specific virus permits application of the procedure to any target bacterium, mycoplasma, fungus or protozoa (G. A. Wistreich and M. D. Lechtman. 1984. "Microbiology", 4th edition, pp. 306–337. MacMillan Publishing Company New York.).

A. Preparation of Labelled Bacteriophages and Reporter Molecule

As previously mentioned, an important feature of the present invention resides in the ability to use intensely labelled virus particles with high specific attachment activity to the target microorganisms. Virus particles rely on chemical functional groups (usually amine or carboxylic acid groups) located on the attachment recognition site of the virus to form a linkage to the specific receptor site on a target microorganism. Conventional labelling processes use amine and carboxylic acid groups to conjugate proteins. Thus, when these conventional processes are used to label a virus, most of the functional groups on the attachment recognition site become conjugated to the label and to each other, and are thus inactivated.

Active sites at the virus attachment recognition site are protected from inactivation in the present invention through the introduction of an entirely different chemical functional group onto the virus. Examples of chemical functional groups which can be used for this purpose include, but are not limited to, sulfhydryl, aldehyde and alcohol groups. To attach any of these new functional groups to the virus, it is first necessary to know whether the chemical functional group at the virus attachment recognition site is an amine, a carboxylic acid or some other chemical functional group. If, for example, it is necessary to protect the amine group, then attachment of the new chemical functional group to the virus is carried out via the carboxylic acid group. Conversely, to protect the carboxylic acid group, attachment is carried out via the amine group. Cross-linkages between amine and carboxylic acid groups located in close proximity to each other on the same or neighboring virus particles are prevented by using an extreme molar excess of the chemical compound containing the new functional group. Examples of such chemical compounds include: mercaptoethylamine (for attaching sulfhydryl groups via carboxylic acid groups on the virus); thioglycollic acid (for attaching sulfhydryl groups via amine groups on the virus); ethanolamine (for attaching alcohol groups via carboxylic acid groups on the virus); and glucuronic acid (for attaching aldehyde groups via amine groups on the virus).

This procedure will be described in more detail in the context of labelling a Salmonella-specific bacteriophage ("phage") with biotin and detecting the resulting virus/microorganism complexes with an avidin-horseradish peroxidase ("AV-HRPO") conjugate. This procedure is equally applicable to the labelling of any virus with biotin, or with a different label, or detection of target-specific virus/target microorganism complexes using a different enzyme or non-enzyme marker.

1. Attachment of Sulfhydryl Groups to Phage

Salmonella-specific bacteriophage No. P-023 ("phage") was suspended in 20 mM MOPS/NaCl buffer pH 7.5 at a concentration of approximately $10^{11}$ phage/mL Five milliliters of phage suspension were combined with 190 mg mercaptoethylamine hydrochloride and 50 μL of 1N NaOH. Ten milligrams of 1-ethyl-3-(3-dimethylaminopropyl) carbodiimide ("CDI") and 1.2 mg of N-hydroxysuccinimide ("NHS") were dissolved together in 80 μL of the same buffer and added to the phage suspension. The mixture was incubated 4 hours at 35° C., the phage recovered by polyethylene glycol precipitation and resuspended in the same buffer. The sulfhydryl-labelled phage were stored at 4°-6° C.

2. Conversion of Attachment Site on Biotin from Carboxyl to Amine

Two hundred and fifty milligrams of D-biotin were dissolved in 4.0 mL of water containing 0.5 mL diaminoethane and the pH adjusted to <10.0 with 1N HCl. Thirty-six milligrams of NHS and 300 mg of CDI were dissolved together in 1.0 mL of 0.2M MOPS buffer, pH 7.5 and then added to the biotin/diaminoethane solution. The pH was adjusted to approximately 7.5 and the solution was incubated 4 hours at 35° C. The solution was evaporated to dryness at 50° C. and the resulting powder washed four times with cold methanol. The powder was evaporated to dryness at 50° C. and stored in dry form at 4°-6° C.

3. Reduction of Sulfhydryl Groups on Phage Prior to Biotin Attachment

Fifteen milligrams of dithiothreitol were added to 5 mL of the sulfhydryl-labelled phage suspension and the mixture was incubated 90 minutes at 35° C. The mixture was then passed through a Sephadex G100 gel filtration column to remove excess dithiothreitol, and the phage were eluted with freshly-reduced 20 mL MOPS/NaCl/EDTA buffer, pH 7.0. The phage suspension was stored in a tightly closed container at 4°-6° C. and used within one hour of preparation.

4. Attachment of Modified Biotin to freshly-reduced phage

One-half milligram of succinimidyl 4-(p-maleimidophenyl) butyrate ("SMPB") was dissolved in 250 μL of dimethyl formamide. Forty milligrams of modified biotin were dissolved in 200 μL of 20 mM MOPS/NaCl, pH 7.5 added to the SMPB solution, and incubated 30 minutes at room temperature with gentle shaking. The entire volume was added to the entire volume of freshly-reduced phage and the mixture was incubated 30 minutes at room temperature with gentle shaking. The biotin-labelled phage were then cleaned using two sequential polyethylene glycol precipitations, resuspended in 5 mL phosphate buffered saline containing thimerosal and stored at 4°-6° C.

5. Preparing Reporter Molecule [Avidin-Horseradish Peroxidase Conjugate ("AV-HRPO")]

Two milligrams of horseradish peroxidase (RZ>3.0) were dissolved in 1 mL water. One hundred microliters of a 0.8M $NaIO_4$ solution were added to the enzyme and the mixture incubated 30 minutes at room temperature with gentle shaking. The reaction was stopped by passing the mixture through a Sephadex G50 gel filtration column and eluting with saline. Three hundred eighty microliters of the eluted enzyme solution were combined with 0.4 mg of avidin and 710 μL saline. Twenty microliters of 0.2M Na-carbonate buffer pH 9.5 were added to raise the pH to 9.5 and the mixture was incubated for two hours at room temperature with gentle shaking. One hundred microliters of a freshly-prepared 0.4% solution of $NaBH_4$ were added and the reaction mixture was incubated for 2 hours at 4°-6° C. The reaction was terminated by passing the mixture through a Sephadex G50 gel filtration column and eluting in phosphate buffered saline, containing thimerosal. The eluted AV-HRPO conjugate was stored at 4°-6° C.

B. Description of Test Kit Protocol

The use of the test kit will be illustrated using as example the detection of a specific target microorganism in a sample of urine.

1. Ten milliliters of urine are placed in a reaction vial (see FIG. 1) containing the appropriate lyophilized labelled target-specific virus. The contents are mixed to ensure uniform distribution of the virus throughout the sample, and the vial is incubated for one hour at 35°-37° C.

2. The correct volume of reporter molecule solution is added to the reaction vial and the contents mixed. The reaction vial is incubated for an additional period of time (depending on the reporter molecule) at 35°-37° C.

3. The top and bottom caps 11 are removed from the capture vial (see FIG. 2) and the entire contents of the reaction vial are poured into the capture vial. The liquid is drained through both the sieve-like filter cloth 7 and the capture filter material 10 by application of a pressure gradient achieved either by applying positive pressure at the top of the capture vial or negative pressure (vacuum) at the bottom of the vial.

4. The top portion of the capture vial 4 containing the filter cloth is discarded, and the lower portion of the capture vial 5 containing the capture filter material is washed with 10 mL of buffer, which flows through the capture filter material under a pressure gradient as described in 3, above.

5. A solution comprising an enzyme substrate and/or enhancer and/or developer is added into the lower portion of the capture vial and allowed to remain in contact with the capture filter material for a period of time and under conditions conducive to detection of the label material contained in the labelled virus/target microorganism complexes trapped on the capture filter material. The reaction may manifest itself either as a precipitate on the surface of the capture filter material or as a change in color in the solution itself. In the former case, the solution is filtered through the capture filter material by means of applying a pressure gradient as described in 3, above; in the latter case, the intensity of reaction in the solution either is read visually or is quantified by using a colorimeter or a spectrophotometer set to the appropriate wavelength.

C. Examples

The process will be illustrated using as an example differentiation between *Salmonella typhimurium* and *Kiebsiella pneumoniae* by a biotin-labelled Salmonella-specific phage.

Cultures of *S. typhimurium* and *K. pneumoniae* were grown in broth culture overnight at 35° C. and heated for 10 minutes at 80° C. to kill the cells. The were then diluted 10-fold into fresh broth tempered to 35° C. The following four combinations were prepared.

VIAL 1: 1 mL *S. typhimurium* + 100 μL biotin-labelled phage

VIAL 2: 1 mL *K. pneumoniae* + 100 μL biotin-labelled phage

VIAL 3: 1 mL broth + 100 μL biotin-labelled phage

VIAL 4: 1 mL broth.

All four vials were incubated for 1 hour at 35° C. Twenty-five microliters of AV-HRPO were added to each vial and the vials incubated an additional 15 minutes at 35° C. The contents of each vial were diluted with an equal volume of 0.2M Na-carbonate/0.5% Tween 80, and the entire volume filtered through a 1 cm diameter spot on a 0.45 micron microporous membrane filter. Each spot was washed by filtering 10 mL of the carbonate/Tween buffer and then placed in 3 mL of a substrate solution (hydrogen peroxide and 2,2'-azinobis(3-ethylbenzthiazoline) sulfonic acid in 0.05M Na-citrate. pH 5.0). The enzyme reaction was allowed to proceed at room temperature for 30 minutes and the resulting color intensities were read in a spectrophotometer using a 600 nm wavelength and a 1 cm path. The intensities resulting from this experiment were:

VIAL 1: 0.33
VIAL 2: 0.23
VIAL 3: 0.18
VIAL 4: 0.225

In another experiment, the labelled virus/microorganism complexes were captured using a 0.65 micron microporous membrane filter. All other parameters were held constant. The results were:

VIAL 1: 0.385
VIAL 2: 0.23
VIAL 3: 0.16
VIAL 4: 0.12.

The foregoing describes and illustrates the preferred embodiment of the present invention. In another embodiment, the capture vial (see FIG. 2) consists of the lower chamber only, eliminating the upper chamber and sieve-like filter cloth. This embodiment is useful for testing particulate-free samples such as waters, many beverages and some clinical specimens (such as clear urine samples).

In certain circumstances (e.g., urine screening or testing for some food-borne pathogens), interpretation of the significance of a finding depends on determining both the identity of a microorganism and the approximate concentration of the microorganism in the original sample. To obtain this information, in yet another embodiment, several different dilutions or volumes of a sample homogenate can be tested, enabling this invention to be used when evaluation of a sample depends on knowing the approximate numbers of target microorganisms present.

In still another embodiment, the biotin-avidin system is replaced by a hapten-anti-hapten system. In such a case, the biotin-labelled virus is replaced with hapten-labelled virus. and the avidin-conjugated reporter molecule (e.g., alkaline phosphatase) is replaced with anti-hapten-conjugated reporter molecule.

Another embodiment comprises labelling the virus directly with a color or fluorescent dye molecule. In this embodiment, no substrate or developer solution would be required. The result can be read directly on the capture filter material immediately following the buffer rinse step.

In yet another embodiment, the pressure gradient is achieved by using a vacuum filtration manifold comprising a plurality of openings, each opening dimensioned to receive and retain the base of one capture vial. The manifold allows application of negative pressure to any one opening, or any combination of openings simultaneously, allowing several samples to be handled conveniently at the same time.

In yet another embodiment, the reaction vial is not used, and the entire process is carried out in the capture vial. Contact between the labelled target-specific virus and the target microorganism may be carried out in the fluid sample contained within the capture vial, or else the fluid sample may be filtered through the capture filter material, and the labelled target-specific virus brought into contact with the target microorganisms trapped on the capture filter material.

The foregoing elaboration has been offered to promote an appreciation and understanding of the disclosed device and no unnecessary limitations should be assumed therefrom.

What is claimed is:

1. A process for attaching a label to a virus such that active binding sites present on the virus are prevented from being blocked or otherwise inactivated, comprising:
   (a) selecting a label having a first active functional group attached thereto;

(b) combining a second active functional group, which is nonreactive with the active binding sites of the virus, with the virus under conditions such that the second active functional group attaches to sites on the virus other than the active binding sites of the virus and the active binding sites of the virus remain unreacted;

(c) attaching a chemical bridging molecule to the first active functional group attached to the label to produce a label/bridge with a free end that is reactive with the second active functional group of the virus but unreactive with the active binding sites of the virus; and (d) combining the label/bridge with the virus under conditions such that the free end of the label/bridge attaches to the second active functional group of the virus and the active binding sites of the virus remain unreacted.

2. A process as in claim 1, wherein said label is biotin.

3. A process as in claim 1, wherein said first active functional group on said label is an amine group.

4. A process as in claim 1, wherein said second active functional group on said virus is a sulfhydryl group.

5. A process as in claim 1, wherein said chemical bridge is a heterobifunctional cross-linker.

6. A process as in claim 1, wherein said chemical bridge is a homobifunctional cross-linker.

7. A process as in claim 1, wherein said first active functional group on said label is a carboxyl group.

8. A process for detection of specific microorganisms comprising:

(a) contacting a labelled target-specific virus produced by the process of claim 1 wherein said virus has been labelled in a manner specifically designed to protect the active binding sites present on the virus from being blocked or otherwise inactivated during the labelling procedure, with a fluid to be tested for the presence of a target microorganism for a time sufficient to permit binding of said virus with said target microorganisms, if present;

(b) collecting any labelled virus/target microorganism complex obtained in (a) on a solid phase;

(c) draining the fluid and washing the solid phase to remove everything other than any labelled virus/target microorganism complex; and (d) determining the presence of labelled virus on the solid phase.

9. A process as in claim 8, wherein said label for said labelled virus is selected from the group consisting of enzymes, color dyes, fluorescent dyes, chemiluminescent dyes, radioactive labels and molecules capable of binding a secondary label selected from the group consisting of enzymes, color dyes, fluorescent dyes, chemiluminescent dyes and radioactive labels.

10. A process as in claim 8, wherein said label is a label which is detected by immersing the solid phase in a solution containing a means of detecting the label present on the virus, and wherein step (d) of claim 8 consists of immersing said solid phase in a solution containing a means of detecting the label.

11. A process as in claim 8, wherein said solid phase is in the form of a filter.

12. A process as in claim 8 wherein step (a) further comprises contacting any labelled virus/target microorganisms complexes with a secondary label capable of being captured by the label present on the virus.

13. A process for detection of a target microorganisms comprising:

(a) bringing in contact in a reaction vessel a labelled target-specific virus produced by the process of claim 1, wherein said virus has been labelled in a manner specifically designed to protect the active binding sites present on the virus from being blocked or otherwise inactivated during the labelling procedure, with a fluid sample or homogenate of a solid sample to be tested for the presence of a target microorganism for a time sufficient to permit the formation of labelled target-specific virus/target microorganism complexes;

(b) bringing in contact the resultant fluid of (a) in a capture vessel with a solid matrix comprising a filter material capable of capturing labelled virus/target microorganism complexes while releasing non-complex components of the resultant fluid;

(c) rinsing and draining fluids from the filter material; and (d) contacting the filter material with an agent capable of reacting with the label on any labelled virus/target microorganism complex to produce a detectable reaction.

14. A process as in claim 13, wherein said reaction vessel is a test tube.

15. A process as in claim 13, wherein said filter material is a membrane filter.

16. A process as in claim 13, wherein said filter material is a microporous membrane filter of pore size equal to or larger than 0.45 microns.

17. A process as in claim 13, wherein said filter material has a porosity capable of allowing the passage of smaller non-virus/microorganisms complex material while retaining the larger labelled virus/target microorganism complexes.

18. A process as in claim 13, wherein said filter material is a microporous membrane filters of pore size of 0.8 to 1.2 microns.

19. A process as in claim 13, wherein said capture vessel contains a detachable portion containing a filter cloth capable of trapping visible particulate matter while permitting flow-through of any labelled virus/target microorganism complexes to the filter material.

20. A process as in claim 13, wherein said filter material is low-protein binding.

21. A process for detection of specific microorganisms comprising:

(a) passing a fluid to be tested for the presence of a target microorganism through a solid phase capable of retaining the target microorganism;

(b) contacting the solid phase with a with a fluid containing a labelled target-specific virus produced by the process of claim 1 for a time sufficient to permit binding of said virus with said target microorganism, if present, wherein said virus has been labelled in a manner specifically designed to protect the active binding sites present on the virus from being blocked or otherwise inactivated during the labelling procedure;

(c) draining the fluid and washing the solid phase to remove non-virus/microorganism complex material while retaining any labelled virus/target microorganism complexes; and (d) determining the presence of labelled virus on the solid phase.

* * * * *